(12) United States Patent
Scott et al.

(10) Patent No.: US 12,004,802 B2
(45) Date of Patent: Jun. 11, 2024

(54) DEVICES, SYSTEMS, AND METHODS FOR CONTROLLED VOLUME ABLATION

(71) Applicant: Boston Scientific Scimed, Inc., Maple Grove, MN (US)

(72) Inventors: Serena Scott, Worcester, MA (US); Mingxiang Xu, Wayland, MA (US); Hong Cao, Maple Grove, MN (US); Carolina Villarreal, Hopedale, MA (US); Christopher Watson, Lincoln, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 649 days.

(21) Appl. No.: 16/984,779

(22) Filed: Aug. 4, 2020

(65) Prior Publication Data
US 2021/0038298 A1 Feb. 11, 2021

Related U.S. Application Data

(60) Provisional application No. 62/882,841, filed on Aug. 5, 2019.

(51) Int. Cl.
| | |
|---|---|
| A61B 18/14 | (2006.01) |
| A61B 18/00 | (2006.01) |
| A61B 18/12 | (2006.01) |

(52) U.S. Cl.
CPC ...... *A61B 18/1492* (2013.01); *A61B 2018/00214* (2013.01); *A61B 2018/00577* (2013.01);
(Continued)

(58) Field of Classification Search
CPC ...... A61B 18/1492; A61B 2018/00214; A61B 2018/00577; A61B 2018/00613;
(Continued)

(56) References Cited

U.S. PATENT DOCUMENTS

| 6,048,329 A | 4/2000 | Thompson et al. |
|---|---|---|
| 8,221,407 B2 | 7/2012 | Phan et al. |

(Continued)

FOREIGN PATENT DOCUMENTS

| WO | 9510318 A1 | 4/1995 |
|---|---|---|
| WO | 2004100813 A2 | 11/2004 |

OTHER PUBLICATIONS

"Tumor Ablation Enhancement by Combining Radiofrequency Ablation and Irreversible Electroporation: An In Vitro 3D Tumor Study" Zhang, B., Yang, Y., Ding, L. et al. Ann Biomed Eng (2019) 47: 694. https://doi.org/10.1007/s10439-018-02185-x.

*Primary Examiner* — Christopher A Flory
(74) *Attorney, Agent, or Firm* — Seager, Tufte & Wickhem, LLP (57) ABSTRACT

The present disclosure relates generally to the field of medical devices. In particular, the present disclosure relates to devices, systems, and methods for controlled volume ablation of tissue. In one example, a catheter may include an elongated member having a distal end extending along a longitudinal axis. A first electrode may extend along the elongated member. The first electrode may have a distal portion arranged on a circumferential surface about the longitudinal axis at the distal end. A second electrode may extend along the elongated member. The second electrode may have a distal portion arranged on the circumferential surface about the longitudinal axis at the distal end of the elongated member. A sheath may be slidably disposed about the elongated member. The sheath may be configured to change position by sliding along the member to insulate a portion of one or both of the first and second electrode.

10 Claims, 6 Drawing Sheets

(52) U.S. Cl.
CPC ............... *A61B 2018/00613* (2013.01); *A61B 2018/126* (2013.01); *A61B 2018/1435* (2013.01); *A61B 2018/1467* (2013.01)

(58) Field of Classification Search
CPC ...... A61B 2018/126; A61B 2018/1435; A61B 2018/1467
See application file for complete search history.

(56) References Cited

U.S. PATENT DOCUMENTS

| | | | |
|---|---|---|---|
| 9,011,430 B2 | 4/2015 | Habib | |
| 9,039,699 B2 * | 5/2015 | Jackson | A61B 18/1492 606/41 |
| 2002/0087208 A1 * | 7/2002 | Koblish | A61B 18/1492 606/41 |
| 2002/0111617 A1 | 8/2002 | Cosman et al. | |
| 2003/0050637 A1 * | 3/2003 | Maguire | A61N 7/02 606/41 |
| 2003/0060820 A1 * | 3/2003 | Maguire | A61N 7/02 606/41 |
| 2003/0125726 A1 * | 7/2003 | Maguire | A61N 7/02 606/41 |
| 2004/0010249 A1 * | 1/2004 | Truckai | A61B 18/14 606/49 |
| 2005/0107781 A1 * | 5/2005 | Ostrovsky | A61B 18/14 606/41 |
| 2008/0097429 A1 | 4/2008 | McClurken | |
| 2008/0188912 A1 * | 8/2008 | Stone | A61F 7/12 606/192 |
| 2013/0165990 A1 * | 6/2013 | Mathur | A61N 1/06 607/101 |
| 2014/0378966 A1 * | 12/2014 | Haverkost | A61B 18/1492 606/41 |
| 2015/0025525 A1 * | 1/2015 | Willard | A61B 18/16 606/34 |
| 2015/0141982 A1 * | 5/2015 | Lee | A61B 5/6853 606/41 |
| 2015/0141987 A1 * | 5/2015 | Caplan | A61B 18/1492 606/41 |
| 2016/0143689 A1 * | 5/2016 | Ditter | A61B 5/287 606/46 |
| 2018/0214204 A1 | 8/2018 | Karmarkar | |
| 2019/0183372 A1 | 6/2019 | Ruppersberg | |
| 2020/0390496 A1 * | 12/2020 | Houden | A61B 90/37 |

* cited by examiner

DEVICES, SYSTEMS, AND METHODS FOR CONTROLLED VOLUME ABLATION

PRIORITY

This application claims the benefit of priority under 35 USC § 119 to U.S. Provisional Patent Application Ser. No. 62/882,841, filed Aug. 5, 2019, which is incorporated by reference herein in its entirety and for all purposes.

FIELD

The present disclosure relates generally to the field of medical devices. In particular, the present disclosure relates to devices, systems, and methods for controlled volume ablation of tissue.

BACKGROUND

Lesions are any type of abnormal tissue of an organism that may result from disease or trauma. Cancerous tumors are an example of abnormal tissue. It is often desirous to disrupt, e.g., ablate, a lesion within the body. Lesions may take on various sizes and shapes. An ablation catheter having discrete electrode bands forming an ablation volume when activated may not provide an ablation volume, shape, or uniformity of energy appropriate for the lesion.

It is with respect to these considerations that the devices, systems, and methods of the present disclosure may be useful.

SUMMARY

The present disclosure, in its various aspects, is directed generally to medical devices, and more specifically to tissue ablation devices, methods, and systems. Embodiments according to the present disclosure, including as described herein, may decrease complications around tissue ablation procedures, such as undesirable ablation of non-targeted tissues. In an aspect, a catheter for controlled volume ablation may include an elongated member having a distal end and extending along a longitudinal axis. A first electrode may extend along the elongated member. The first electrode may have a distal portion arranged on a circumferential surface about the longitudinal axis on the distal end of the elongated member. A second electrode may extend along the elongated member. The second electrode may have a distal portion arranged on the circumferential surface about the longitudinal axis at the distal end of the elongated member. A sheath may be slidably disposed about the elongated member. The sheath may be configured to change position by sliding along the member to insulate a portion of one or a portion of both electrodes from the surrounding tissue.

In various embodiments described here or otherwise, the distal portion of the first electrode and the distal portion of the second electrode may each form a helix about the circumferential surface of the elongated member. Turns of the helix of the distal portion of the first electrode may be interspersed with turns of the helix of the distal portion of the second electrode. The distal portion of the first electrode may include a first radial band about the longitudinal axis. A plurality of first electrode portions may extend from the first band distally toward a distal tip of the elongated member. The distal portion of the second electrode may include a second radial band about the longitudinal axis. A plurality of second electrode portions may extend from the second band proximally toward the first band such that the first electrode portions alternate and overlap with the second electrode portions radially about the circumferential surface of the elongated member. The distal portion of the first electrode and the distal portion of the second electrode may each form a series of alternating radial bands along the longitudinal axis. The first electrode may have a proximal portion that extends along a surface of the elongated member to the distal portion of the first electrode. The second electrode may have a proximal portion that extends along the surface of the elongated member to the distal portion of the second electrode. The distal portion of the second electrode may be adjacent the distal portion of the first electrode. The distal end of the elongated member may include an expandable member. The distal portion of the first electrode may include a first radial band about the longitudinal axis proximal to the expandable member. A plurality of first electrode portions may extend from the first band distally toward a distal tip of the catheter. The distal portion of the second electrode may include a second radial band about the longitudinal axis distal to the expandable member. A plurality of second electrode portions may extend from the second radial band proximally toward the first radial band such that the plurality of first electrode portions alternate with the plurality of second electrode portions about the circumferential surface of the elongated member. An inflation lumen may extend along the elongated member and in fluid communication with the expandable member. A thermal sensor may be disposed on the distal end of the elongated member. The thermal sensor may be configured to provide feedback for controlling a supply of energy to the first and second electrodes to maintain a desired temperature. A lumen may extend through the elongated member and may be in fluid communication with an aperture at the distal end of the catheter.

In an aspect, a catheter for controlled volume ablation may include an elongated member having a distal end and a longitudinal axis. A plurality of electrodes may extend along the elongated member. Each electrode of the plurality of electrodes may terminate in a distal band about a circumferential surface of the elongated member. Each of the distal bands of the plurality of electrodes may alternate along the longitudinal axis and may be configured to be controlled as an active electrode or a return electrode. Each electrode of the plurality of electrodes may be configured to be independently controlled.

In various embodiments, the plurality of electrodes may be selectively activatable to control the length of the ablation volume such that at least two electrodes activated together along the longitudinal axis may form a predetermined ablation volume. Each electrode of the plurality of electrodes may extend internally along the elongated member to each distal band of the plurality of electrodes.

In an aspect, a method for controlling an ablation volume may include delivering a distal end of an elongated member of a catheter with electrodes to a target tissue. At least two electrodes of the plurality of electrodes may be activated to create an ablation volume about the activated electrodes. The ablation volume may be adjusted by selectively exposing a portion of the activated electrodes to the target tissue. Energy may be delivered from the exposed portion of the activated electrodes to the target tissue.

In various embodiments, the catheter may include a sheath that may be slidably disposed about the elongated member. The length of the ablation volume may be adjusted by proximally retracting the sheath along the member from about the exposed portion of the activated electrodes. A length of an expandable member may be expanded at the distal end of the elongated member into contact with the target tissue. The expanded length of the expandable member may substantially match a desired length of the ablation volume for the target tissue. A number of distal-most electrodes along a longitudinal axis of the catheter may be activated such that the number of distal-most electrodes forms a length along the longitudinal axis that corresponds to a desired ablation volume for the target tissue. The activated electrodes may form a length along the longitudinal axis that matches a desired length of ablation volume for the target tissue. Radio frequency ablation or irreversible electroporation may be performed when activating the electrodes. A temperature of the target tissue may be monitored and may be maintained at about 90° C., at a level specified by the user, or otherwise as clinically desired.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the embodiments described. The terminology used herein is only for the purpose of describing particular embodiments and is not intended to be limiting. Unless otherwise defined, all technical terms used herein have the same meaning as commonly understood by one of ordinary skill in the art to which the disclosure belongs.

As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

As used herein, the conjunction "and" includes each of the structures, components, portions, or the like, which are so conjoined, unless the context clearly indicates otherwise, and the conjunction "or" includes one or the others of the structures, components, portions, or the like, which are so conjoined, singly and in any combination and number, unless the context clearly indicates otherwise.

The detailed description should be read with reference to the drawings, which are not necessarily to scale, depict illustrative embodiments, and are not intended to limit the scope of the invention.

Endoscopic procedures may involve insertion of an endoscope through a natural orifice into an organ or lumen of the body to examine and treat the interior of the organ or lumen. Treatment probes, such as ablation catheters, can be inserted through a lumen of an endoscope to treat lesions in the body. Although embodiments of the present disclosure may be described here with specific reference to ablation of lesions with bipolar electrode catheters, it should be appreciated that such devices, systems, and methods may be used with a variety of instruments and for a variety of other tissues, body passageways, organs and/or cavities, such as the vascular system, urogenital system, upper gastrointestinal system, lower gastrointestinal system, respiratory system, and the like.

In various embodiments, an ablation volume may be illustrated or described two-dimensionally while a catheter is illustrated or described three-dimensionally. An ablation volume may be depicted in a single plane, e.g., along a longitudinal axis, however, in use the two-dimensional ablation volume fills a three-dimensional, e.g., revolved around the longitudinal axis.

Figure 1:
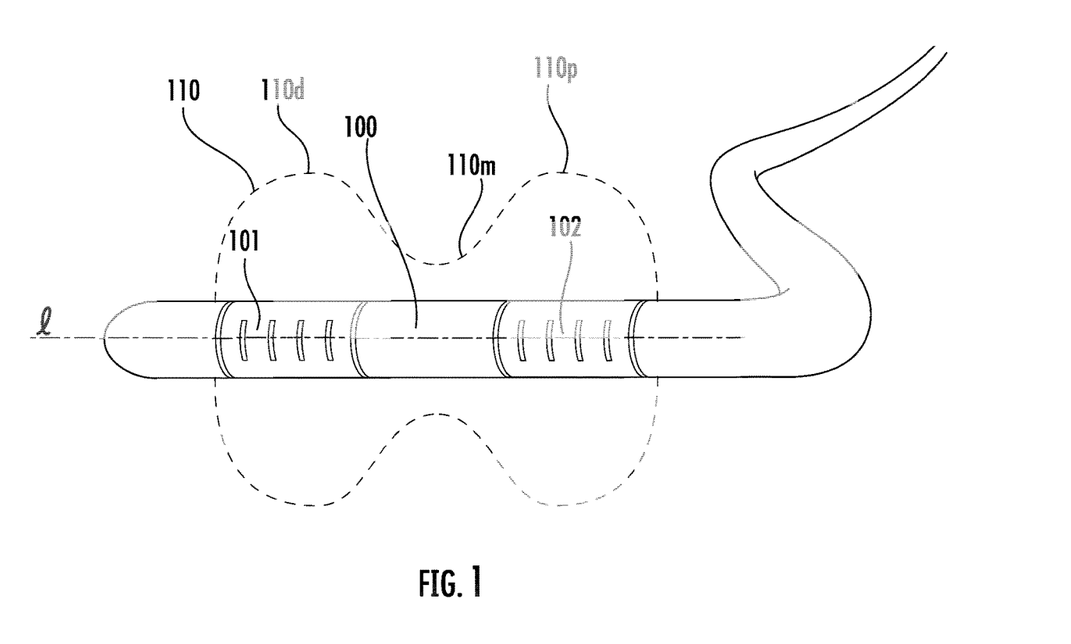
FIG. 1 illustrates an exemplary bipolar electrode catheter and the ablation volume of a catheter with a fixed number and position of electrodes.

Referring to FIG. 1, an ablation catheter 100 is illustrated. The catheter 100 includes bipolar electrodes made up of an active distal electrode 101 and a return proximal electrode 102. When activated, the electrodes 101, 102 create an ablation volume 110 in target tissue. The volume 110 has a varied profile from a proximal end 110p to a distal end 110d of the field 110 across the electrodes 101, 102, e.g., a "dumbbell" shape. The proximal end 110p about the proximal electrode 102 and the distal end 110d about the distal electrode 101 each have a diameter perpendicular to a longitudinal axis 1 of the catheter that is greater than a diameter of the mid-portion 110m of the volume 110 between the electrodes 101, 102. The profile of the volume 110 is not substantially uniform along a length of the catheter 100, which may not be desirable for treating a target tissue. The ablation volume 110 is depicted as a two-dimensional cross-section of a three-dimensional volume that revolves about the longitudinal axis 1. For example, a medical professional may deliver the catheter 100 to the target tissue such that the electrodes 101, 102 are at least partially aligned with a length of the target tissue. The electrodes 101, 102 may then be activated such that the ablation volume 110 extends into the target tissue. However, because of the varied profile of the ablation volume 110, the target tissue may not receive a substantially uniform treatment. For example, portions of the target tissue corresponding with the ends 110p, 110d of the ablation volume 110 may receive more ablation energy than portions of the target tissue corresponding with the mid-portion 110m of the ablation volume 110. Additionally, because of the varied profile of the ablation volume 110, tissue surrounding the target tissue not meant to receive any ablation energy may be undesirably ablated. Further, the ablation volume 110 along the longitudinal axis 1 may not be adjusted. A medical professional may be unable to tailor the ablation volume 110, e.g., the length and/or diameter of the ablation volume 110, to correspond with the target tissue.

In various embodiments, a bipolar electrode arrangement may be provided at a distal end of a catheter capable of delivering a high electric field in micro to nano-second pulses or a radiofrequency current. The electrodes are coupled with an energy source, e.g., an irreversible electroporation (IRE), reversible electroporation (RE), or radiofrequency (RF) generator, located outside of the body of the patient. Energy application may be dependent upon the size or type of the tissue to be ablated or the type of procedure employed. For example, RF ablation may be employed for clearing strictures and tissue debulking while IRE may be employed for ablation of tumors near blood vessels by ceasing cell or tissue function without breaking down the cell or tissue scaffolding. Electrode design and placement for use in IRE embodiments of the present invention are substantially the same as for RF embodiments described herein. Insulative properties of a catheter sheath may depend on the energy used with the electrodes, e.g., such that activated electrodes within a sheath do not contribute to an ablation volume created by the activated electrodes that are exposed (i.e., not within the sheath). Ablation energy may take the form of resistive heating electrodes.

Figure 2:
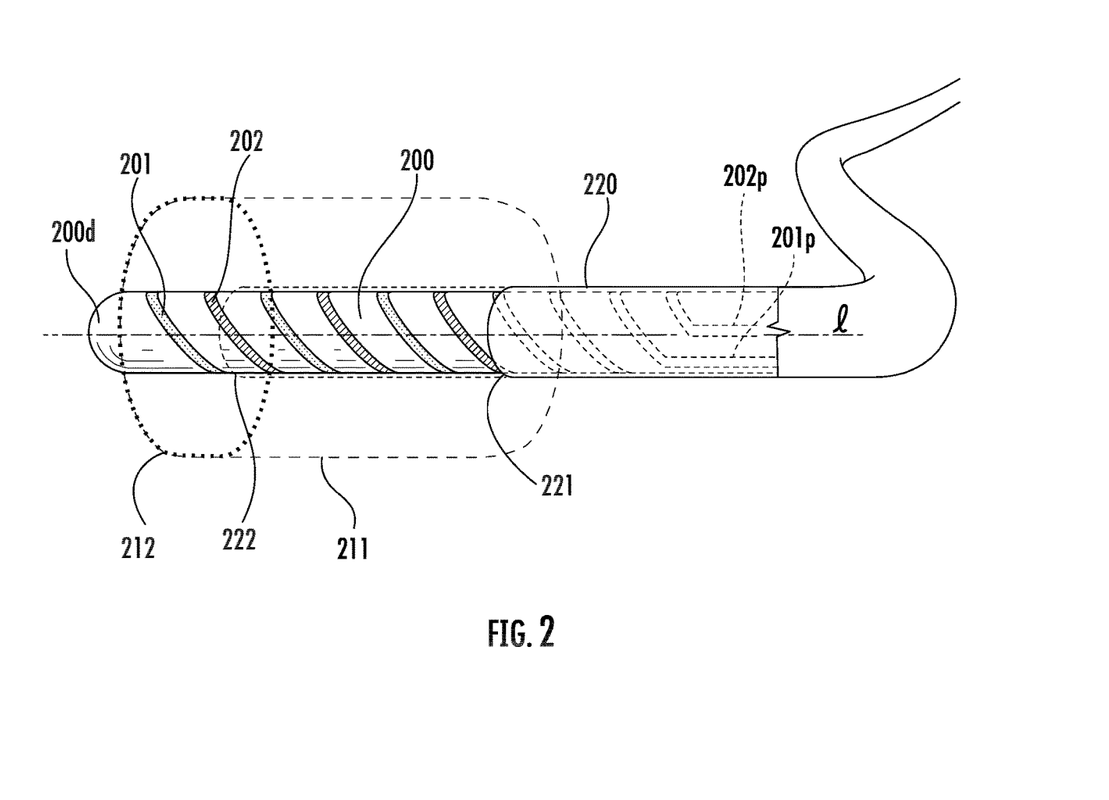
FIG. 2 illustrates a catheter for controlled volume ablation having two electrodes, in accordance with an embodiment of the present disclosure.

With reference to FIG. 2, a catheter for controlled volume ablation is illustrated, which includes an elongated member 200 having a distal end 200d and extending along a longitudinal axis 1 along its length. A first electrode 201 extends along the elongated member 200 and has a distal portion arranged about the longitudinal axis 1 on the distal end 200d of the elongated member 200. A second electrode 202 also extends along the elongated member 200 and has a distal portion arranged about the longitudinal axis 1 on the distal end 200d of the elongated member 200. In various embodiments, one or more electrodes may be active while one or more other electrodes are return electrodes. Depending on circuit arrangement and coupling to an energy source, the electrodes may switch from active to return electrodes. The distal portion of the first electrode 201 and the distal portion of the second electrode 202 each form a helix about the longitudinal axis 1 and about a circumference of the elongated member 200. Turns of the helix of first electrode 201 are interspersed with turns of the helix of the second electrode 202. A helix may have a pitch and a number of turns that may depend on an intended use. For example, a smaller pitch may have a more even distribution of energy but may be limited by material properties, such as the dielectric strength of the insulation of the helix and the peak voltage from the energy source, whereas a helix with a larger pitch may have a more uneven distribution of energy, etc. A pitch may be about 0.1 millimeters to about 10 millimeters. An electrical trace width may be about 0.1 millimeters to about 10 millimeters. A number of turns of a helix may be about 1 to about 100. For example, a helix may have a pitch of about 0.5 millimeters (about 0.02 inches) to about 1.0 millimeters (about 0.04 inches). For another example, a helix may have an about 0.020-inch-wide electrical trace, with an about 0.120 inch pitch, and about 5 to about 18 turns. Helical electrodes extend along the longitudinal axis 1 more so than the electrodes 101, 102 of FIG. 1 and are therefore less likely to produce the ablation volume shape 110 of FIG. 1. A proximal portion 201p, 202p of each of the electrodes 201, 202 may extend proximally along the surface of the elongated member 200 and substantially parallel with the longitudinal axis 1. Alternatively, the proximal portions 201p. 202p may extend along the interior of the elongated member 200. A sheath 220 is slidably disposed longitudinally and rotationally about the elongated member 200. The sheath 220 is configured to insulate a portion of one or both of the first electrode 201 and the second electrode 202 from a surrounding tissue. The position of the sheath 220 may be changed by sliding along the elongated member 200 to expose portions of the first and second electrodes 201, 202 to adjust an ablation volume. For example, the sheath 220 may be located at a first position 221 where activating the electrodes 201, 202 would create a first ablation volume 211. The sheath 220 may be moved to a second position 222 where activating the electrodes 201, 202 would create a second ablation volume 212 having a smaller volume than the first ablation volume 211. The ablation volumes 211, 212 are each depicted as two-dimensional cross-sections of a three-dimensional volume that revolves about the longitudinal axis 1. A medical professional may adjust the position of the sheath 220 with respect to the elongated member 200 and electrodes 201, 202 to adjust the ablation volume along the length of the elongated member 200 as desired for the target tissue to achieve any number, length, shape, etc., of ablation volumes.

Figure 3:
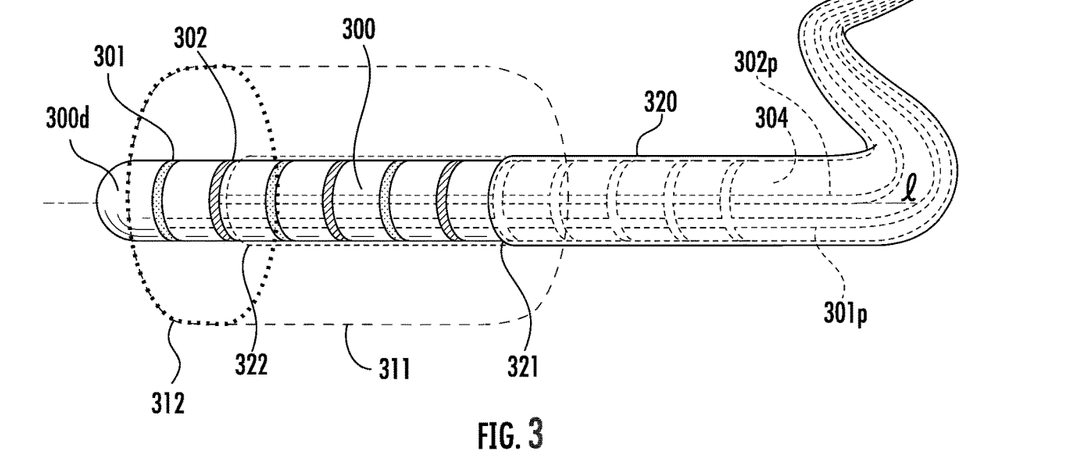
FIG. 3 illustrates a catheter for controlled volume ablation having two electrodes, in accordance with an embodiment of the present disclosure.

With reference to FIG. 3, a catheter for controlled volume ablation is illustrated, which includes an elongated member 300 with a first electrode 301 and a second electrode 302. Each electrode 301, 302 has a distal portion arranged about a longitudinal axis 1 on a distal end 300d of the elongated member 300. The distal portion of the first electrode 301 and the distal portion of the second electrode 302 each form a series of alternating bands along the longitudinal axis 1. The longitudinally spaced bands of the electrodes 301, 302 may allow for more flexibility of the elongated member 300 compared to the helical electrodes 201, 202 along the longitudinal axis l of FIG. 2. A proximal portion 301p, 302p has a conductive connection with each of the electrodes 301, 302 that extends proximally within a lumen 304 of the elongated member 300. A sheath 320 is slidably disposed about the elongated member 300. The sheath 320 is configured to insulate a portion of one or both of the first electrode 301 and the second electrode 302 from a surrounding tissue. A position of the sheath 320 may be changed by sliding the sheath 320 along the elongated member 300 to expose portions of the first and second electrodes 301, 302 to adjust an ablation volume. For example, the sheath 320 may be at a first position 321 where activating the electrodes 301, 302 creates a first ablation volume 311. The sheath 320 may instead be moved to a second position 322 where activating the electrodes 301, 302 creates a second ablation volume 312 having a smaller volume than the first ablation volume 311. The ablation volumes 311, 312 are each depicted as two-dimensional cross-sections of a three-dimensional volume that revolves about the longitudinal axis l. A medical professional may adjust the position of the sheath 320 with respect to the elongated member 300 and electrodes 301, 302 to adjust the ablation volume along the length of the elongated member 300 as desired for the target tissue to achieve any number, length, shape, etc., of ablation volumes.

Figure 4:
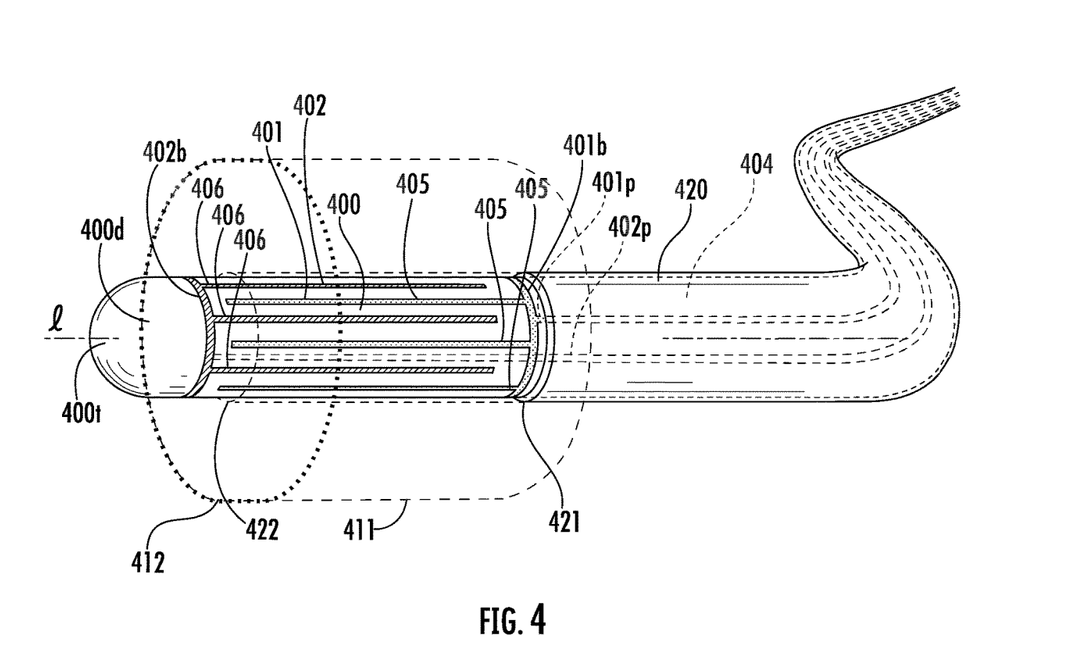
FIG. 4 illustrates a catheter for controlled volume ablation having two electrodes, in accordance with an embodiment of the present disclosure.

With reference to FIG. 4, a catheter for controlled volume ablation is illustrated, which includes an elongated member 400 with a first electrode 401 and a second electrode 402. Each electrode 401, 402 has a distal portion arranged about a longitudinal axis l on the distal end 400d of the elongated member 400. The distal portion of the first electrode 401 has a first band 401b on a circumferential surface of the elongated member 400 about the longitudinal axis l and a plurality of first electrode portions 405 extending in a direction substantially parallel along the longitudinal axis l from the first band 401b toward a tip 400t of the elongated member 400. The distal portion of the second electrode 402 has a second band 402b on the circumferential surface of the elongated member 400 about the longitudinal axis l and a plurality of second electrode portions 406 extending in a direction substantially parallel to the longitudinal axis l from the second band 402b toward the first band 401b. The first electrode portions 405 alternate and overlap with the second electrode portions 406 about the circumferential surface of the elongated member 400 in a circumference that is normal to the longitudinal axis l. The plurality of first and second electrode portions 405, 406 extend along the longitudinal axis l more so than the electrodes 101, 102 of FIG. 1 and are therefore less likely to produce the ablation volume 110 shape of FIG. 1. The plurality of first and second electrode portions 405, 406 extending along the longitudinal axis l may increase a stiffness of a distal portion of the elongated member 400 (compared to the electrodes 101, 102 of FIG. 1) that may assist a medical professional with delivering and positioning of the distal end of the elongated member 400. A proximal portion 401p of the first electrode 401 extends proximally along the surface of the elongated member 400, but may alternatively have a conductive connection with the first band 401b and extend proximally within a lumen 404 of the elongated member 400. A proximal portion 402p of the second electrode 402 has a conductive connection with the second band 402b and extends within the lumen 404 of the elongated member 400. A sheath 420 is slidably disposed about the elongated member 400. The sheath 420 is configured to insulate a portion of one or both of the first electrode 401 and the second electrode 402 from a surrounding tissue. A position of the sheath 420 may be changed by sliding along the elongated member 400 to expose portions of the first and second electrodes 401, 402 to adjust an ablation volume. For example, the sheath 420 may be at a first position 421 where activating the electrodes 401, 402 creates a first ablation volume 411. The sheath 420 may instead be moved to a second position 422 where activating the electrodes 401, 402 creates a second ablation volume 412 having a smaller volume than the first ablation volume 411. The ablation volumes 411, 412 are each depicted as two-dimensional cross-sections of a three-dimensional volume that revolves about the longitudinal axis l. A medical professional may adjust the position of the sheath 420 with respect to the elongated member 400 and electrodes 401, 402 to adjust the ablation volume along the length of the elongated member 400 as desired for the target tissue to achieve any number, length, shape, etc., of ablation volumes. The electrode portions 405, 406 may be further divided into more electrodes than just the electrodes 401, 402 such that certain electrode portions 405, 406 can be selectively activated to create an ablation volume that is not circumferentially about the longitudinal axis l, e.g., to treat a lesion on a portion of a body lumen with a half circumferential ablation volume rather than the fully circumferential volumes 411, 412. Such additional electrodes dividing up the electrode potions allow for controlled ablation volume in axial and radial directions in any desired portion of the circumference around the longitudinal axis.

Figure 5A:
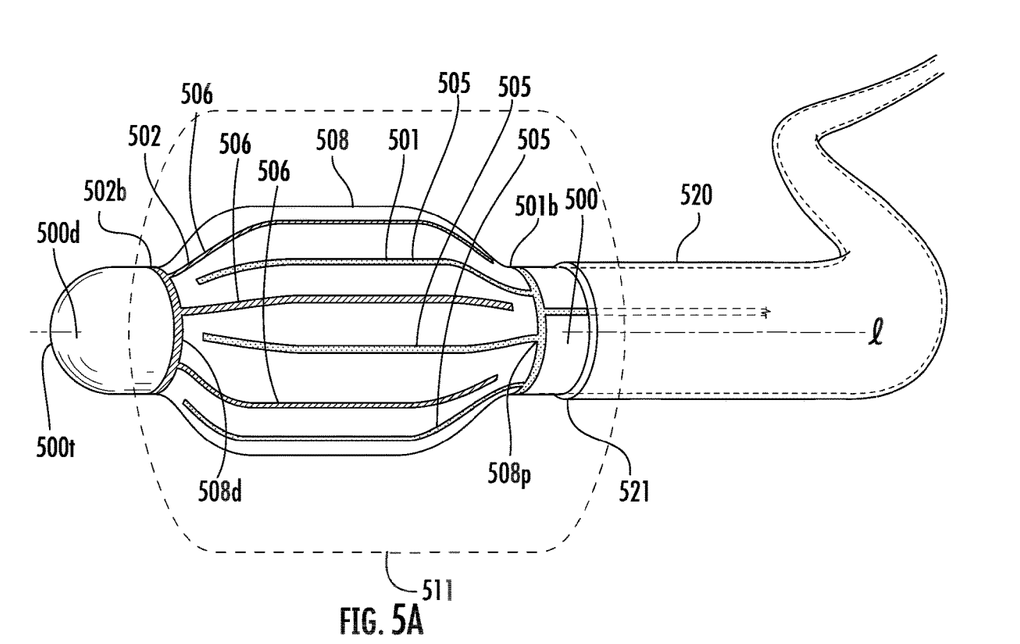
FIG. 5A illustrates a catheter for controlled volume ablation having two electrodes and an expandable member, in accordance with an embodiment of the present disclosure.
Figure 5B:
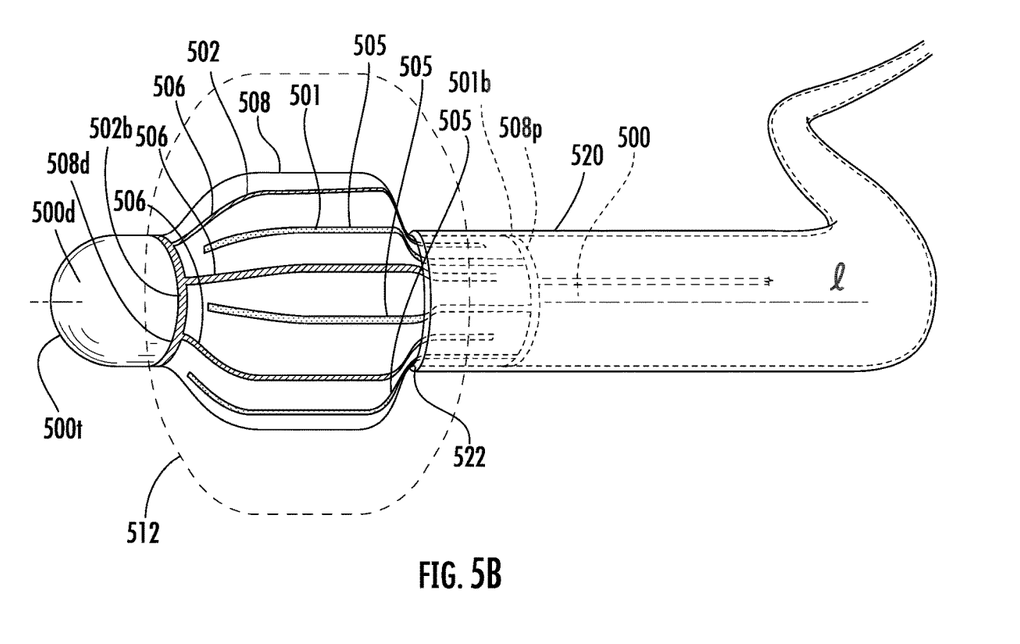
FIG. 5B illustrates the catheter of FIG. 5A with a sheath for controlling an ablation volume of exposed electrodes and inflation of the expandable member, in accordance with an embodiment of the present disclosure.

With reference to FIGS. 5A and 5B, a catheter for controlled volume ablation is illustrated, which includes an elongated member 500 having a longitudinal axis l and an expandable member 508, e.g., a non-compliant inflatable balloon, at a distal end 500d of the elongated member 500. A first electrode 501 has a distal portion with a first band 501b on a circumferential surface of the elongated member 500 about the longitudinal axis l that may be proximal to the expandable member 508. The first electrode 501 includes a plurality of first electrode portions 505 extending in a direction substantially parallel with the longitudinal axis l from the first band 501b toward a tip 500t of the elongated member 500. A second electrode 502 has a distal portion with a second band 502b on the circumferential surface of the elongated member 500 about the longitudinal axis l that may be distal to the expandable member 508. The second electrode 502 includes a plurality of second electrode portions 506 extending in a direction substantially parallel on the longitudinal axis l from the second band 502b toward the first band 501b such that the plurality of first electrode portions 505 alternate and overlap with the plurality of second electrode portions 506 about the circumferential surface of the elongated member 500 in a circumference that is normal to the longitudinal axis l. The first electrode portions 505 and second electrode portions 506 do not extend about a circumference of the elongated member 500 and may therefore more easily expand about the elongated member 500 compared to, e.g., the electrodes 101, 102 of FIG. 1. An inflation lumen (not illustrated) along the elongated member 500 may be used to expand the expandable member 508. The expandable member 508 may be expanded (e.g., as illustrated in FIG. 5A) to bring the electrodes 501, 502 into the proximity of the target tissue. The expandable member 508 may be expanded to maintain patency in a body lumen containing the target tissue, e.g., in order to access the target tissue. A sheath 520 is slidably disposed about the elongated member 500. The sheath 520 is configured to insulate a portion of one or both of the first electrode 501 and the second electrode 502 from a surrounding tissue. A position of the sheath 520 may be changed by sliding along the elongated member 500 to expose portions of the first and second electrodes 501, 502 to adjust an ablation volume and an expanded volume of the expandable member 508. For example, the sheath 520 in position 521 permits the activated electrodes 501, 502 to form a first ablation volume 511 and permits the expandable member 508 to form the expanded volume illustrated in FIG. 5A. The sheath 520 in position 522 permits the activated electrodes 501, 502 to form a second ablation volume 512 and permits the expandable member 508 to form the expanded volume as illustrated in FIG. 5B that is smaller along the longitudinal axis l than the first ablation volume 511 of and the expanded volume of the expandable member 508 of FIG. 5A. The ablation volumes 511, 512 are each depicted as two-dimensional cross-sections of a three-dimensional volume that revolves about the longitudinal axis l.

In various of the above and other embodiments, expanding an expandable member into contact with a body lumen may be done to position a device within a patient, for example, at the substantially central point of the body lumen, such that electrodes of a device are substantially equidistant from the walls of the body lumen (i.e., centered within the lumen) or positioned as some other predetermined distance or orientation with respect to the body lumen. The expandable member may also expand into contact with the walls of a body lumen.

Figure 6:
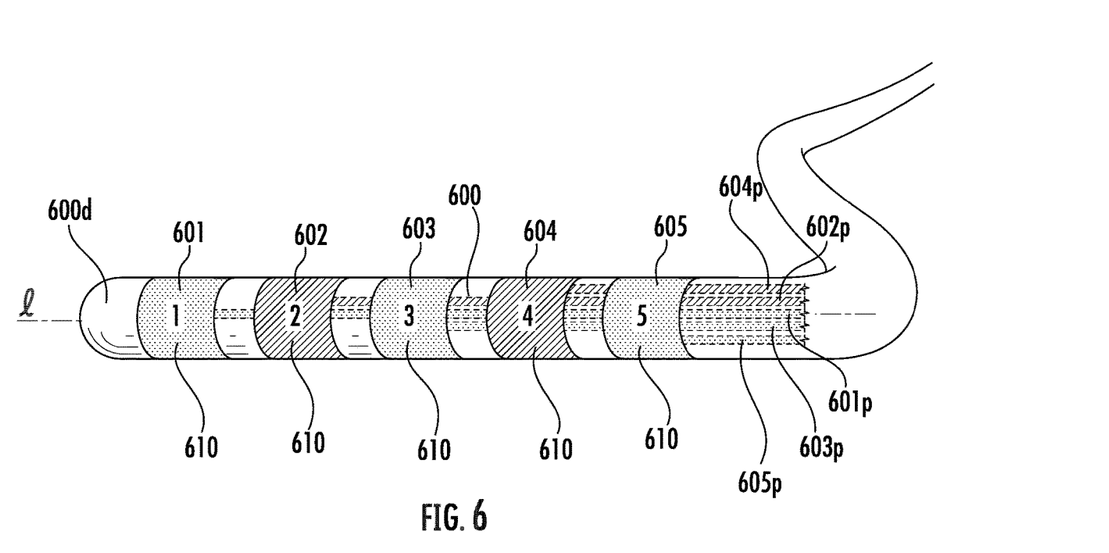
FIG. 6 illustrates a catheter for controlled volume ablation having five electrodes, in accordance with an embodiment of the present disclosure.

With reference to FIG. 6, a catheter for controlled volume ablation is illustrated, which includes an elongated member 600 having a distal end 600d and extending along a longitudinal axis l. Five electrodes 610 extend along the elongated member 600. Although five electrodes 610 are illustrated, any number of electrodes may be used, e.g., 3, 4, 6, 8, 10, 15, 20, 50, etc. Each electrode 610 terminates in a distal end about a circumference of the elongated member 600. The electrodes 610 are evenly spaced apart from adjacent electrodes 610 along the longitudinal axis l in FIG. 6, however this spacing between adjacent electrodes 610 may vary and may relate to the ablation volume. The electrodes 610 may be arranged to alternate along the longitudinal axis l between, e.g., active electrodes 601, 603, 605 and return electrodes 602, 604. Proximal portions 601p, 602p, 603p, 604p, 605p, of each electrode 610 are conductively connected to each electrode 610 and extend proximally within and/or along the elongated member 600. Any of the electrodes 610 may be an active electrode 610 or a return electrode 610 depending on how an energy source is coupled to the proximal portions 601p, 602p, 603p, 604p, 605p, of each electrode 610. The electrodes 610 may be independently activated, e.g., such that some of the electrodes 610 are active and some are not. The electrodes 610 may be activatable at different energies. Some or all of the electrodes 610 may be activatable to control an ablation volume produced from the electrodes 610. For example, the first 601 and second 602 electrodes 610 may be activated to form an ablation volume. As another example, the first 601, second 602, and third 603 electrodes 610 may be activated to form a larger ablation volume than that of the previous example. As another example, the third electrode 603, fourth electrode 604, and fifth electrode 605 may be activated to form an ablation volume substantially equivalent in size to the previous example, but at a location farther from the distal end 600d of the elongated member 600 than in the previous example. As another example, all of the electrodes 610 of an elongated member 600 may be activated to form a larger ablation volume than with the previous examples. As another example, non-adjacent electrodes 610 may be activated together along the longitudinal axis to form an ablation volume unique from the previous examples such as the first 601 and fourth 604 electrodes. Other combinations of selectively and/or independently activating the electrodes 610 to produce varying ablation volumes can be utilized and may be selected depending on the target tissue. In various embodiments, various ablation volumes, e.g., a spherical, ellipsoidal, or a combination, etc., may be desirable. Independent electrodes may be configured to receive various energy densities and/or waveforms that may differ across the independent electrodes. For example, electrode 603 may transfer the highest energy density through a continuous waveform while electrodes 601 and 605 transfer lower energy densities via a pulsed waveform.

Figure 7:
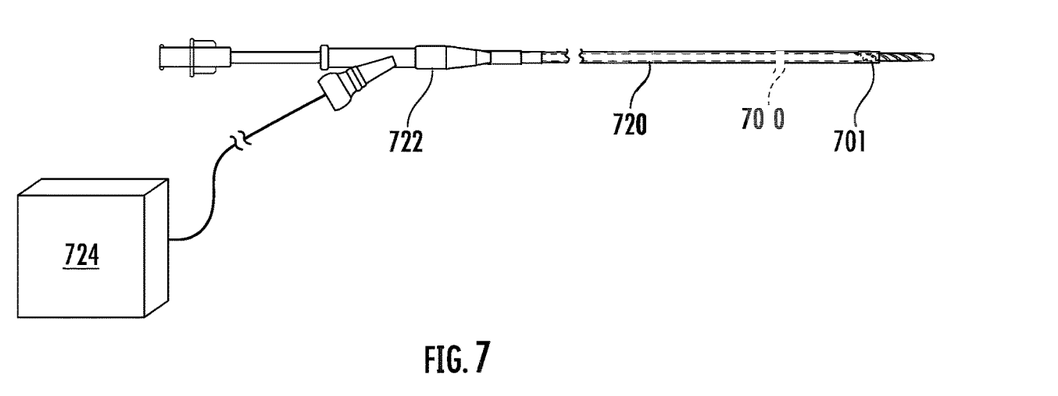
FIG. 7 illustrates a system for controlled volume ablation, in accordance with an embodiment of the present disclosure.

With reference to FIG. 7, a system for controlled volume ablation is illustrated, which includes a catheter having an elongated member 700. The elongated member 700 includes electrodes 701 about a circumference of the elongated member 700. The catheter includes a sheath 720 slidably disposed about the elongated member 700. The sheath 720 may slide along the member 700 to insulate a portion of one or more electrodes from a surrounding tissue. The catheter includes a handle 722 that may be used to manipulate the elongated member 700, the sheath 720, and/or other devices extending through the catheter. The catheter is coupled to an energy source 724. The handle 722 may control the activation of the electrodes 701.

In various embodiments, a catheter may include geometries and/or additional features for monitoring, visualizing, or controlling an ablation volume. For example, a catheter may include a lumen extending through the catheter and in fluid communication with an aperture at a distal end of the catheter that may be configured to accept a device (e.g., a guidewire) and/or a fluid (e.g., a contrast, a drug, a cooling saline, an inflation fluid). A catheter may include a sensor (e.g., a thermal sensor) that may be disposed along the distal end of the catheter and may be configured to provide feedback for controlling a supply of energy (e.g., to maintain a temperature of a target tissue).

In various embodiments, a method for controlling an ablation volume may include delivering a distal end of an elongated member of a catheter with electrodes to a target tissue. At least two electrodes of the plurality of electrodes may be activated to create an ablation volume about the activated electrodes. The ablation volume may be adjusted by selectively exposing a portion of the activated electrodes to the target tissue. Energy may be delivered from the exposed portion of the activated electrodes to the target tissue. The catheter may include a sheath that may be slidably disposed about the elongated member. The length of the ablation volume may be adjusted by proximally retracting the sheath along the member from about the exposed portion of the activated electrodes. A length of an expandable member may be expanded at the distal end of the elongated member into contact with the target tissue. The expanded length of the expandable member may substantially match a desired length of the ablation volume for the target tissue. A number of distal-most electrodes along a longitudinal axis of the catheter may be activated such that the number of distal-most electrodes forms a length along the longitudinal axis that corresponds to a desired ablation volume for the target tissue. The activated electrodes may form a length along the longitudinal axis that matches a desired length of ablation volume for the target tissue. Radio frequency ablation or irreversible electroporation may be performed when activating the electrodes. A temperature of the target tissue may be monitored and may be maintained at a targeted level, such as about 90° C. or otherwise clinically desired.

In various embodiments, different materials may be selected for various parts of a device or assembly. For example, various portions of a catheter body or a device body may be made up of a stainless steel, a cobalt alloy, a platinum alloy, ceramic, a combination thereof, or the like. Electrodes may be made up of gold, platinum, steel, nickel, titanium, copper, niobium, silver, other electrical conductors, a combination thereof, or the like. An expandable member may be made up of PET, PEEK, nylon, polyurethane, Pebax, stainless steel, or nitinol, or a combination thereof, or the like. A device may have a coating made up of a urethane, a molded thermoplastic, a thermoplastic urethane, a thermosetting urethane, Pebax, or a thermoplastic elastomer, or a combination thereof, or the like. A sheath may be a tubular polymer, may be made up of a coil or braid reinforced polymer, or may be a polymer encapsulated laser cut metallic tube. A sheath may be provided with or without a lubricious liner, such as PTFE or PFA. An exterior of the sheath may include a lubricious additive, such as Propell, or Kemamide. Polymers for the sheath may include Pebax, urethane, polyimide, polyamide, a combination thereof, or the like. A catheter may be made up of a laminate of stainless-steel tubing, PET heat-shrink tubing, coil-reinforced polymer, such as Pebax, nitinol, or a combination thereof, or the like. One or more of the materials may be laser cut to impart certain properties along the length of the catheter, e.g., flexibility.

All of the devices and/or methods disclosed and claimed herein can be made and executed without undue experimentation in light of the present disclosure. While the devices and methods of this disclosure have been described in terms of preferred embodiments, it will be apparent to those of skill in the art that variations can be applied to the devices and/or methods and in the steps or in the sequence of steps of the method described herein without departing from the spirit and scope of the disclosure. All such similar substitutes and modifications apparent to those skilled in the art are deemed to be within the spirit and scope of the disclosure as defined by the appended claims.

What is claimed is:

1. A catheter for controlled volume ablation, comprising:
   an elongated member having a distal end and extending along a longitudinal axis;
   a first electrode extending along the elongated member, the first electrode having a plurality of distal portions each arranged as a circumferential band on a circumferential surface about the longitudinal axis on the distal end of the elongated member;
   a second electrode extending along the elongated member, the second electrode having a plurality of distal portions each arranged as a circumferential band on the circumferential surface about the longitudinal axis at the distal end of the elongated member such that the portions of the second electrode alternate with the portions of the first electrode along the longitudinal axis, the first and second electrodes creating a first ablation volume when activated while exposed to surrounding tissue; and
   a sheath slidably disposed about the elongated member, the sheath configured to change position by sliding along the member to, during an ablation procedure, insulate a portion of the first electrode and a portion of the second electrode from a surrounding tissue while selectively exposing a portion of the first electrode and a portion of the second electrode to the surrounding tissue, the exposed portions of the first and second electrodes creating a second ablation volume when activated that is less than the first ablation volume.

2. The device of claim 1, wherein the first electrode has a proximal portion that extends along a surface of the elongated member to the distal portion of the first electrode and the second electrode has a proximal portion that extends along the surface of the elongated member to the distal portion of the second electrode.

3. The device of claim 1, wherein the distal portion of the second electrode is adjacent the distal portion of the first electrode.

4. The device of claim 1, wherein the distal end of the elongated member comprises an expandable member.

5. The device of claim 1, further comprising a thermal sensor disposed on the distal end of the elongated member and configured to provide feedback for controlling a supply of energy to the first and second electrodes to maintain a desired temperature.

6. The device of claim 1, further comprising a lumen extending through the elongated member and in fluid communication with an aperture at the distal end of the catheter.

7. A method for controlled volume ablation, comprising:
   deploying a catheter for an ablation procedure, the catheter comprising:
      an elongated member having a distal end and extending along a longitudinal axis,
      a sheath, and
      first and second electrodes extending along the elongated member, each of the first and second electrodes having a plurality of circumferential bands on the distal end of the elongated member, the bands of the first electrode alternating with the bands of the second electrode along the longitudinal axis, the first and second electrodes creating a first ablation volume when activated while exposed to surrounding tissue;
   delivering the distal end of the elongated member of the catheter to a target tissue;
   activating the first and second electrodes;
   during the ablation procedure, adjusting the ablation volume by moving the sheath to selectively expose a portion of the activated first and second electrodes to the target tissue, creating a second ablation volume that is less than the first ablation volume; and
   delivering energy from the exposed portion of the activated electrodes to the target tissue.

8. The method of claim 7, wherein adjusting the ablation volume further comprises proximally retracting the sheath along the member and from about the exposed portion of the activated first and second electrodes.

9. The method of claim 7, further comprising expanding a length of an expandable member at the distal end of the elongated member into contact with the target tissue, the length of the expandable member substantially matching the second ablation volume for the target tissue.

10. The method of claim 7, further comprising performing radio frequency ablation or irreversible electroporation.

* * * * *